(12) United States Patent
Kenny et al.

(10) Patent No.: US 10,564,527 B2
(45) Date of Patent: Feb. 18, 2020

(54) DEVICE AND SYSTEM FOR MAINTAINING A LEVEL HORIZON OF A SUPPORTED CAMERA

(71) Applicants: Francis Kenny, Santa Monica, CA (US); Dennis Emer, Cresskill, NJ (US); Jarred Land, Los Angeles, CA (US); Sallyanne Massimini, Marina Del Rey, CA (US); Robert Stone, Fairview, CA (US)

(72) Inventors: Francis Kenny, Santa Monica, CA (US); Dennis Emer, Cresskill, NJ (US); Jarred Land, Los Angeles, CA (US); Sallyanne Massimini, Marina Del Rey, CA (US); Robert Stone, Fairview, CA (US)

( * ) Notice: Subject to any disclaimer, the term of this patent is extended or adjusted under 35 U.S.C. 154(b) by 0 days.

(21) Appl. No.: 16/378,448

(22) Filed: Apr. 8, 2019

(65) Prior Publication Data

US 2019/0310535 A1 Oct. 10, 2019

Related U.S. Application Data

(60) Provisional application No. 62/655,166, filed on Apr. 9, 2018.

(51) Int. Cl.
*G03B 17/56* (2006.01)
*F16M 11/12* (2006.01)
(Continued)

(52) U.S. Cl.
CPC ............ *G03B 17/561* (2013.01); *F16C 11/06* (2013.01); *F16M 11/125* (2013.01);
(Continued)

(58) Field of Classification Search
CPC ................... F16M 11/12–128; F16M 11/14
(Continued)

(56) References Cited

U.S. PATENT DOCUMENTS

| 3,924,828 A | * | 12/1975 | Epperson | ............... F16M 11/08 |
| | | | | 248/179.1 |
| 4,795,118 A | * | 1/1989 | Kosugi | ............... F16M 11/041 |
| | | | | 248/181.1 |

(Continued)

FOREIGN PATENT DOCUMENTS

| GB | 598280 A | * | 2/1948 | ............... F16F 7/02 |
| JP | 2016095391 A | * | 5/2016 | |

*Primary Examiner* — Clayton E. LaBalle
*Assistant Examiner* — Leon W Rhodes, Jr.
(74) *Attorney, Agent, or Firm* — Continuum Law; Robert P. Cogan

(57) ABSTRACT

A mounting head, a system incorporating the mounting head and a support such as a monopod, and a system including the mounting head, the monopod, and a camera enable a photographer to tilt a monopod or other camera support while maintaining a substantially level horizon of an image. An upper head assembly and a lower head assembly are connectable to the camera and the monopod respectively. The assemblies are interconnected by a universal joint which allows the upper assembly to remain level as roll and pitch vary. A resilient member dampens relative motion of the head assemblies. As a photographer moves the camera to capture a scene, force is transmitted from the photographer's hands via the mounting head through the monopod. The photographer maintains a level horizon as the monopod tilts. A test apparatus enables design of a resilient member for desired interaction with selected classes of equipment.

17 Claims, 10 Drawing Sheets

(51) Int. Cl.
*F16M 11/16* (2006.01)
*F16C 11/06* (2006.01)
*G01N 3/08* (2006.01)
*F16M 11/22* (2006.01)
*F16M 11/14* (2006.01)

(52) U.S. Cl.
CPC ............ *F16M 11/16* (2013.01); *F16M 11/22* (2013.01); *G01N 3/08* (2013.01); *F16M 11/14* (2013.01); *F16M 2200/022* (2013.01)

(58) Field of Classification Search
USPC ........................................................ 396/419
See application file for complete search history.

(56) References Cited

U.S. PATENT DOCUMENTS

| | | | | |
|---|---|---|---|---|
| 7,658,555 | B1* | 2/2010 | Moilanen | G01C 21/18 |
| | | | | 348/373 |
| 8,408,820 | B2* | 4/2013 | Manson | F16M 11/14 |
| | | | | 396/419 |
| 9,052,573 | B2* | 6/2015 | Johnston | G03B 17/561 |
| 9,574,706 | B2* | 2/2017 | Brown | F16M 11/041 |
| 9,874,308 | B2* | 1/2018 | Saika | H04N 5/2328 |
| 2007/0155228 | A1* | 7/2007 | Nama | F16M 11/10 |
| | | | | 439/567 |
| 2012/0106941 | A1* | 5/2012 | Greaves | F16M 11/046 |
| | | | | 396/421 |
| 2018/0038544 | A1* | 2/2018 | Peters | F16M 11/10 |

* cited by examiner

DEVICE AND SYSTEM FOR MAINTAINING A LEVEL HORIZON OF A SUPPORTED CAMERA

CROSS REFERENCE TO RELATED APPLICATIONS

This patent application claims priority to U.S. Provisional Patent Application Ser. No. 62/655,166 filed Apr. 9, 2018, which is incorporated herein by reference in its entirety.

BACKGROUND

Field

The present subject matter relates to a camera mounting head and to a system, the system including the camera mounting head and a support for real time horizon control, for maintaining a horizon level or at another selected angle.

Background

In the arts of cinematography, videography, and photography with virtually any viewing device, a significant requirement is maintaining a level or other image horizon. A photographer may consciously maintain an "off level" shot known in the cinema industry as a "dutch tilt." There has been a need for addressing shortcomings in the prior art, e.g., vibration isolation, control of camera tilt, maneuverability of large, heavy cameras, and ability to control framing. Prior camera supports which avoided making the image angle a function of tilt of the camera support have been complicated, very heavy, difficult to hold, and very expensive. They did not allow for maneuverability in limited spaces, e.g., on a film set. They also did not allow for the camera operator to maintain an invisibility with the camera equipment to avoid distracting the actors or other subjects. For simplicity in the present description, an operator of any device for capturing images is referred to as a photographer. A support mechanism is often used for stability. A monopod, tripod, or dolly are commonly used camera supports. Tripods and dollies provide for stability but are either cumbersome, heavy, and often require a special permit when used on city streets or parks. However, they do not provide a hands-on photographer the ability to move with agility to capture scenes. While many sorts of camera supports may be used, the monopod has become increasingly popular. A benefit of the monopod is the fact that it is a single post type device which supports the weight of the camera without taking up valuable floor space, as would be the case with a tripod. A monopod is a single post device which supports the weight of the camera while minimizing the amount of physical space that the camera and photographer occupy.

On a film or television set, time and space are at a premium. A plurality of camera operators may be employed in close proximity to each other. The subject being recorded often moves in a way requiring the camera operator to adjust their position and maintain desired framing of the subject. Moving the base of a monopod or tilting of a monopod is often undesirable because it may result in jerky motion and reduce the ability to maintain desired framing, and cause the shot to be "off level" with respect to the subject. Moving the monopod's base position would probably make the operator "lose the shot" because of the time it would take to move the monopod. This is especially true in the field of episodic television, news photography, sports photography, wedding photography, fashion photography, feature films, and documentaries where response time to capture the moment is in milliseconds and can make the difference between success or failure.

In order to maintain continuity of a shot, a photographer may keep the base of the monopod in place and tilt the monopod without moving its base position. If the photographer shooting a scene having a level horizon tilts the monopod, a fluid and consistent framing of the subject may be maintained, but there is a loss of level horizon in the captured image. There has been no easy way to maintain a horizon level in real time when shooting unless the photographer used a camera with a horizon level indicator. In the majority of situations, a loss of level horizon is undesirable. It must be compensated for.

A number of software solutions have been provided to compensate for loss of level horizon. Recent feature films, such as Gone Girl, $20^{th}$ Century Fox (2014), have dealt with such "off level" shots by using computer programs to compensate for undesired angular disposition of images. Shots must be "over framed" and shot in a wider format. e.g. shot in 8K reduced to 6K framing within the larger format. These include such software applications as Adobe's After Effects®, Photoshop®, and Premiere Pro®. However, use of postproduction software is expensive. Expense is incurred in use of equipment and in requiring skilled operators. Use of post-production software also introduces time lags into the postproduction process. Such time lags are highly undesirable in an industry where deadlines can be critical.

The method of mating between the monopod and the camera has historically been a solid male/female threaded connection in order to maximize reliability. The predominant prior art form of mounting of a camera to a monopod is a rigid connection. This may be secure, but it presents a drawback. This current state of the art connection method requires the camera operator during image capture to keep the monopod at a 90° angle to the floor. Otherwise, the image captured will not be level. For example, a tilt of the monopod to 95° would create a captured image that was out of level by 5°. The photographer does not have an option to having the captured image being out of level.

Producers have discovered that more work can be achieved in less time using smaller lighter weight equipment. The ability to achieve more work in less time is a precious commodity in the entertainment industry. Support devices for newer cameras have followed suit and also the devices have become more mobile.

Technology has changed the way images are captured, edited, and viewed. Cameras have become smaller in size, weight, with digital sensor size and resolution increasing exponentially. Ten years ago cameras were seven times the weight and size of current cameras. Technological advances have allowed for new and different ways of image acquisition.

There is great pressure to be able to produce more images in a given situation. One published study, James E. Cutting and Ayse Candan, *Shot Durations, Shot Classes, and the Increased Pace of Popular Movies*, Projections, Volume 9, Issue 2, Winter 2015: 40-62, ISSN 1934-9688 (Print), ISSN 1934-9696 (Online), finds that films shot within the last several years have increased use of techniques using more off level shots than in prior years. These techniques produce a higher quantity of shots, each shot being of a shorter duration. The study finds that such techniques have increased the profitability and other measures of success of a film. Long takes are expensive in both rehearsal time and crew time. Facilitating short duration shots allows for decreasing cost of production and of working with newly evolving paradigms in production values.

The prior art has not provided a simple and elegant solution to address the phenomenon of loss of level or other selected horizon while maintaining agility.

U.S. Pat. No. 9,052,573 discloses a video camera motion stabilizing device intended to provide smooth video images as a camera on a monopod is moved. This construction requires a gimbaled system cooperating with a counterweighted monopod. This device is complicated in construction and utilizes costly components, reduces the spontaneity of capturing the moment, and is expensive.

U.S. Pat. No. 8,408,820 discloses a portable leveling camera mount having a platform for mounting a camera, a sensor for detecting an orientation of the platform; and an actuator coupled to move the platform in response to the orientation detected via the sensor. This device requires sensing circuitry and actuator control circuitry. Position compensation cannot be made directly in response to an applied force. Motion must be transformed into signals and then back into motion.

United States Published Patent Application No. 2007/0155228 discloses a device that comprises friction plates that provide rotary damping to a mounted device, e.g. a camera system on a platform, pivoted to a moving arm. As the arm changes attitude, the mount system allows dampened rotary movement of the mounted device about an axis, due to gravity forces. However, this device does not compensate for forces applied directly to the platform and requires an extremely skilled operator.

U.S. Pat. No. 9,874,308 discloses an electronic gimbal with camera and mounting configuration. The gimbal comprises an inertial measurement unit which senses orientation of the camera and uses three electronic motors to manipulate orientation of the camera. This system is complicated and expensive.

United States Published Patent Application No. 2018/0038544 discloses a rotation stabilization device having at least one axis of rotation running through the center of gravity of a camera. A torque converter is situated on at least one axis of rotation between an electric motor and the camera. While this device provides for hands free stabilization, it is also complicated and expensive.

SUMMARY

Briefly stated, in accordance with the present subject matter, there is provided a mounting head. There is a system incorporating the mounting head and a monopod. There is also a system including the mounting head, the monopod, a camera with the mounting head having proper locking mechanisms.

The present subject matter provides a novel solution to a photographer's need to be able to tilt the monopod while maintaining a substantially unchanged horizon. This unique apparatus allows for the mounting head to interact with the monopod to adjust the horizon. It provides omnidirectional horizon correction, vibration isolation, and substantial elimination of dutch angles for the monopod. The apparatus allows for eased maintenance of a level horizon without the need for a horizon level indicator in a camera. A horizon indicator is a useful tool that lets the photographer know if the camera is plumb level but importantly if the device was not being used the horizon indicator would only let the photographer know if they were "off level." This apparatus facilitates maintaining a selected horizon. In one embodiment it may appear similar to an oversized hockey puck. This custom solution is strong and can correct maximum of 15-20° and never separate. "Never separate" relates to the amount of weight put on the device. There is a weight limit for a given mounting head construction. A 500 lb. inverted camera on a nominal camera mount could separate. The mounting head sits between the camera and the monopod. The apparatus is made of specially formulated polymers and aerospace metals. There is an industry standard diameter male thread on top and an industry standard diameter female thread on the bottom.

A mounting head, a system incorporating the mounting head and a support such as a monopod, and a system including the mounting head, the monopod, and a camera enable a photographer to tilt a monopod or other camera support while substantially maintaining an existing horizon of an image. An upper head assembly and a lower head assembly are connectable to the camera and the monopod respectively. The assemblies are interconnected by a universal joint which allows the upper assembly to remain level as roll and pitch vary. A resilient member dampens relative motion of the head assemblies. As a photographer moves the camera to capture a scene, force is transmitted from the photographer's hands via the mounting head through the monopod. The photographer may maintain a level horizon as the monopod tilts. A test apparatus enables design of a resilient member for desired interaction with selected classes of equipment. The monopod and the mounting head form a system in which tilting of the lower cup member by virtue of its connection to the monopod is compensated for by changing its angular displacement to the upper cup displacement. In a further system a camera is rigidly mounted to the upper cup assembly and the support is rigidly mounted to the lower cup assembly.

DETAILED DESCRIPTION

Figure 1:
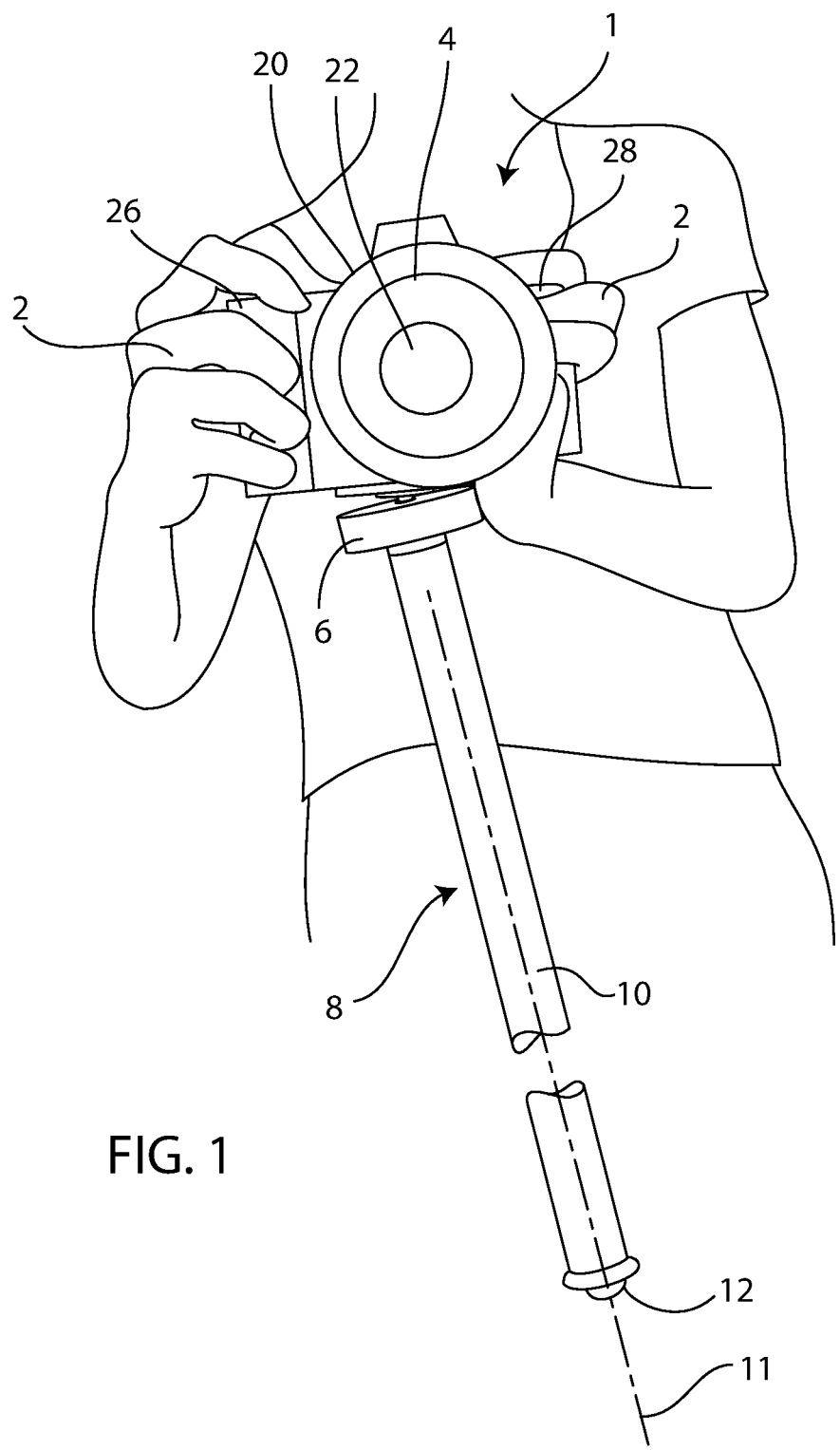
FIG. 1 illustrates a photographer moving a camera transversely while maintaining a monopod foot in position.

In accordance with the present subject matter, a structure is provided which permits a photographer to move a camera changing the roll and pitch of the camera simultaneously. The photographer does not have to move hands to maintain a grip on the camera. A photographer may keep a monopod base in one position while tilting the monopod off level horizon. Even when the monopod is tilted, the photographer may maintain a substantially constant level or other selected horizon. The mounting head provides an omnidirectional coupling between a monopod and a device used for imaging. This device may be, for example, a still camera, a motion picture camera, a set of binoculars, or other device in which an operator creates a frame.

Technology has changed the way images are captured, edited, and viewed. Cameras have become smaller in size, weight, with digital sensor size and resolution increasing exponentially. Ten years ago cameras were seven times the weight and size of current cameras. Technological advances have allowed for new and different ways of image acquisition. However, large, heavy cameras are still employed in the film industry.

As with any technological change, tools that once worked as a system, now became dated and anachronistic. A paradigm shift was created by a cultural lag. Camera support tools previously used to accomplish tasks no longer worked under the new rules of current day production. Smaller locations, use of multiple cameras, cross shooting, more set ups involving more coverage, less time and crew, LED lighting, and smaller budgets required small, high resolution cameras with small support gear, became commonly relied-upon support tools.

The mounting head according to the present subject matter provides omnidirectional horizon correction, vibration isolation, and substantial elimination of dutch angles, i.e., angles of displacement from a level horizon, for the monopod. The apparatus allows for eased maintenance of a level horizon without the need for a horizon level indicator in a camera. Another advantage of use of a monopod is the efficient use of space in comparison to tripods or dollies. Tripods and dollies provide camera stability but are cumbersome, heavy, require additional crew, and often a special permit when used on a street or parks. Expensive mobile support systems such as Steadicam™, Movi®, Ronin®, and Easy Rigs® require expert skill and are only effective for specific type shots. Rarely are those tools used in tandem.

In still photography putting a camera in the right space at the right time defines success. In cinematography, where the majority of content is framed in medium and close ups, moving or stabilizing a camera in real time defines success. Recently, monopods have become a "go to" tool for camera support. They don't require special permits, take up little space, and can be used with a minimum of crew.

A number of photographers may work in close proximity in the often limited space of a set. By facilitating the ease-of-use of a monopod that is tilted in operation, the disadvantages of having to move the foot of a monopod are avoided. The present subject matter provides a novel solution to the photographer's long felt need to have the ability to both tilt a monopod and maintain a level horizon. The mounting head can be used instead of a flat base tripod head.

Moving the monopod's base position would probably make the operator "lose the shot" because of the time it would take to move or adjust the monopod. This is especially true in the field of episodic television, news photography, sports photography, wedding photography, fashion photography, feature films, and documentaries where response time to capture the moment is in milliseconds and can make the difference between success or failure.

But monopods present conundrum. However small the profile locks, knobs, clamps, and twists are necessary to adjust camera height and adjusting height reduces the photographer's ability to maintain desired framing in real time.

In order to solve the problem of real time vertical height adjustment with a monopod, a professional camera support system known under the trademark Steadicam Air was developed by MC4. The Steadicam Air monopod was a two stage monopod housing a gas nitrogen spring activated by a foot pedal. The Steadicam Air allowed for real time vertical camera adjustment with a monopod. But vertical adjustment only solved one of two problems for real time. Horizon control without the use of locks and knobs was still a problem.

The present mounting head, a high viscosity head capable of smoothly supporting a professional camera and lens, was designed to give the photographer/cinematographer real time horizon control when using a monopod. Horizon control is defined as the ability to "maintain or not maintain" a level horizon during framing.

The present mounting head is made from specially formulated polymers and aerospace metals. It allows for silent, fluid, real time camera adjustments up to 18 degrees in any direction during a shot without the need for manipulating mechanical knobs or locks. It aids in finding horizon, dutch tilts, and vibration isolation.

In accordance with the present subject matter it has been found that the mounting head is useful for other camera techniques. One such technique is the cinema verite style. The mounting head reduces unwanted body movements when handholding a camera. It is particularly suitable for feathering panning and tilting shots when a traditional tripod head is used.

The apparatus also has vibration isolation properties that will help reduce unwanted vibrations. Because of its low profile the module also allows the viewing device to be used for extremely low angle shots yet still allow the operator pan and tilt flexibility.

Adjustments to actions or reactions in front of the camera or at the camera have never been faster or more organic. In one form the apparatus has a male ¼"-20 thread top and a female ⅜"-16 on the bottom. The mounting head is a module having means for attachment to a tripod, monopod, rifle viewing device, with a flat horizontal top, in the center having an upright threaded male post protruding in either ⅜"-20 or ¼-20, and a likewise female thread within the bottom flat surface in either ¼"-20 or ⅜"-20. The module is cylindrical in shape measuring diametrically 2¾ inches, and 1½" in height. Two metal collars enclose the module extending from the top and bottom surface. The collars extending from the top of the module is ¼"-20, The collar on the bottom portion of the module has a female ⅜"-16.

Figure 2:
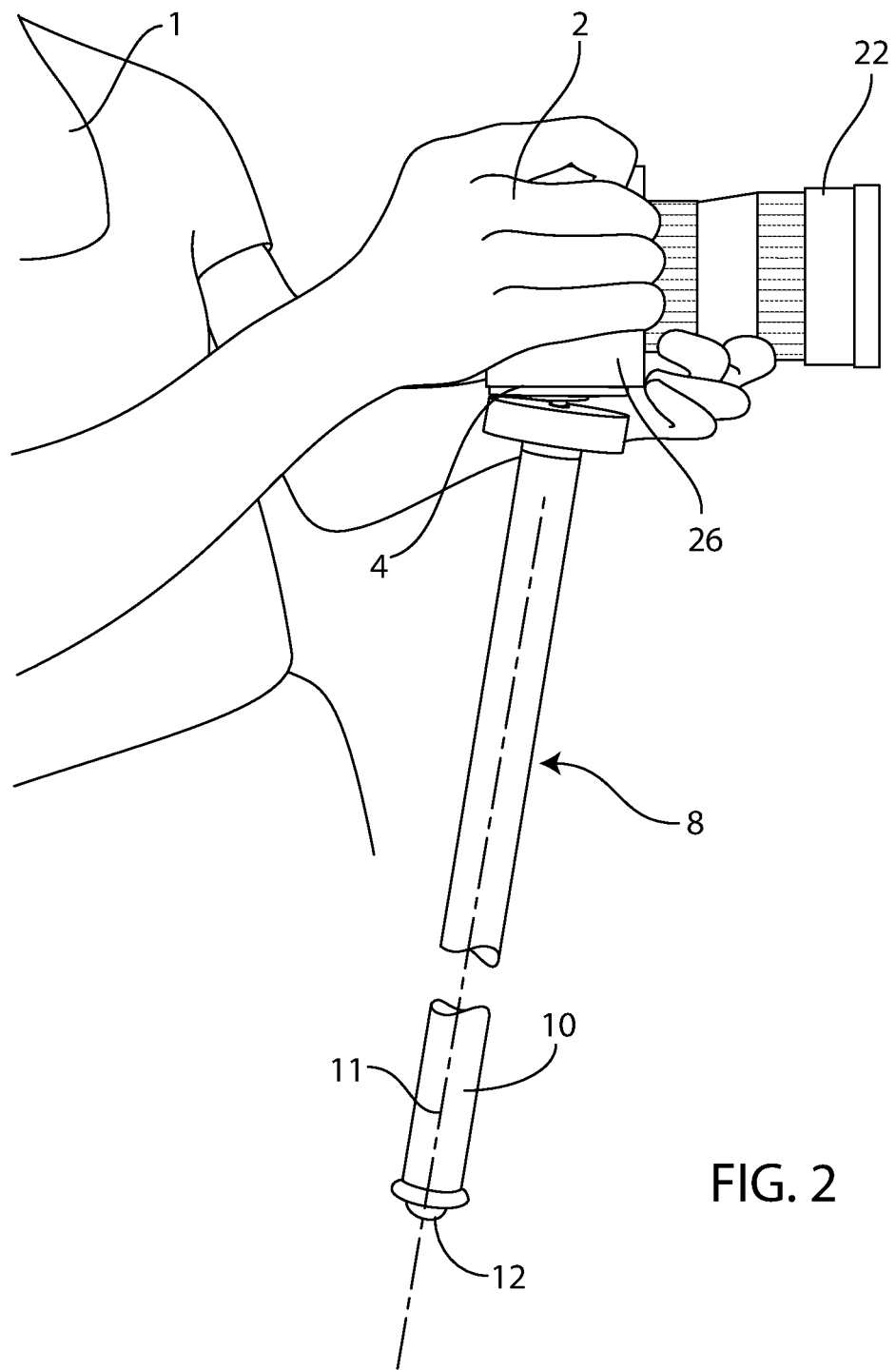
FIG. 2 is an illustration of the photographer utilizing the apparatus and system according to the present subject matter to provide desired pitch of a supported camera.
Figure 3:
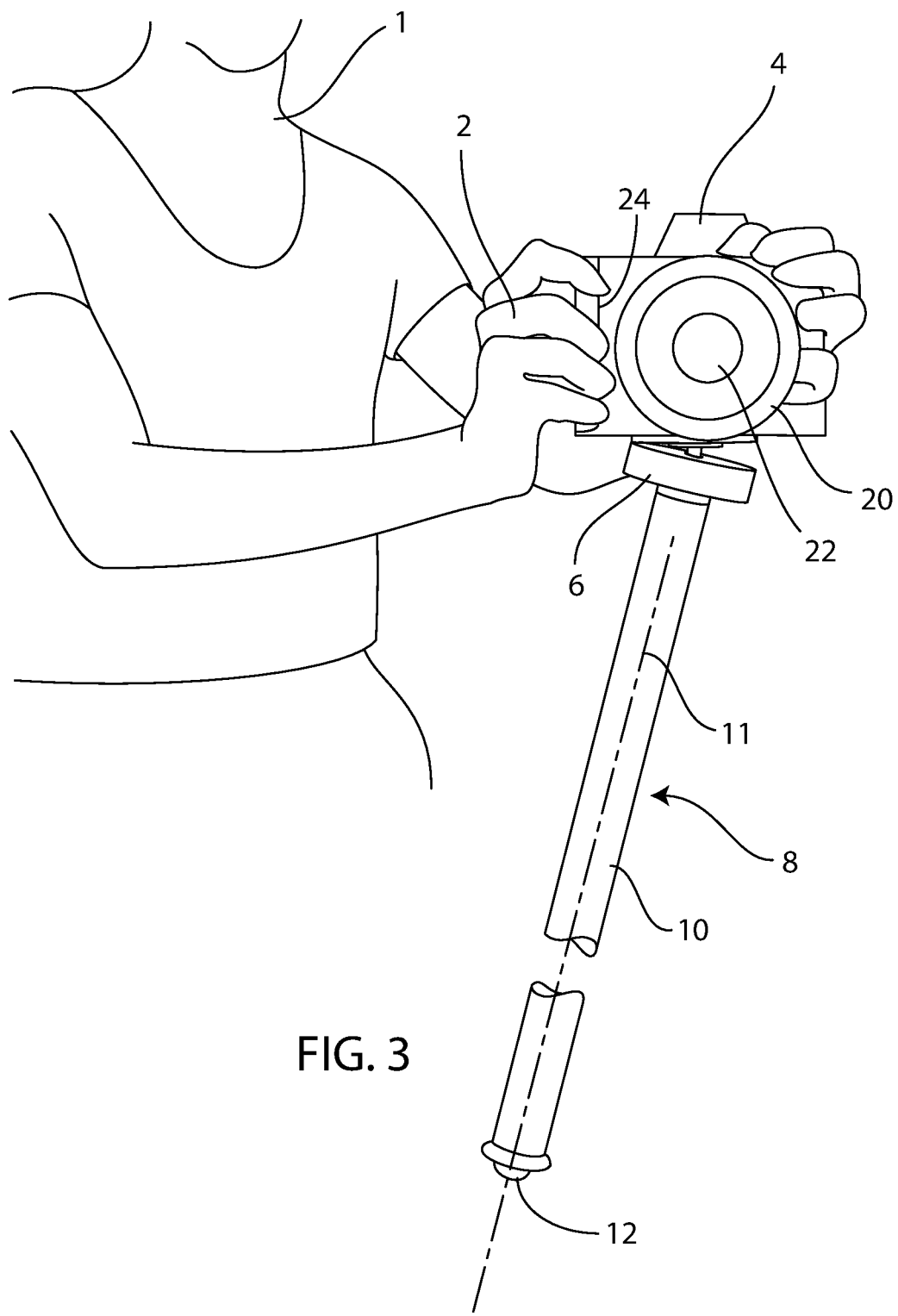
FIG. 3 is an illustration of the photographer utilizing the apparatus and system according to the present subject matter to select yaw of a supported camera.
Figure 4:
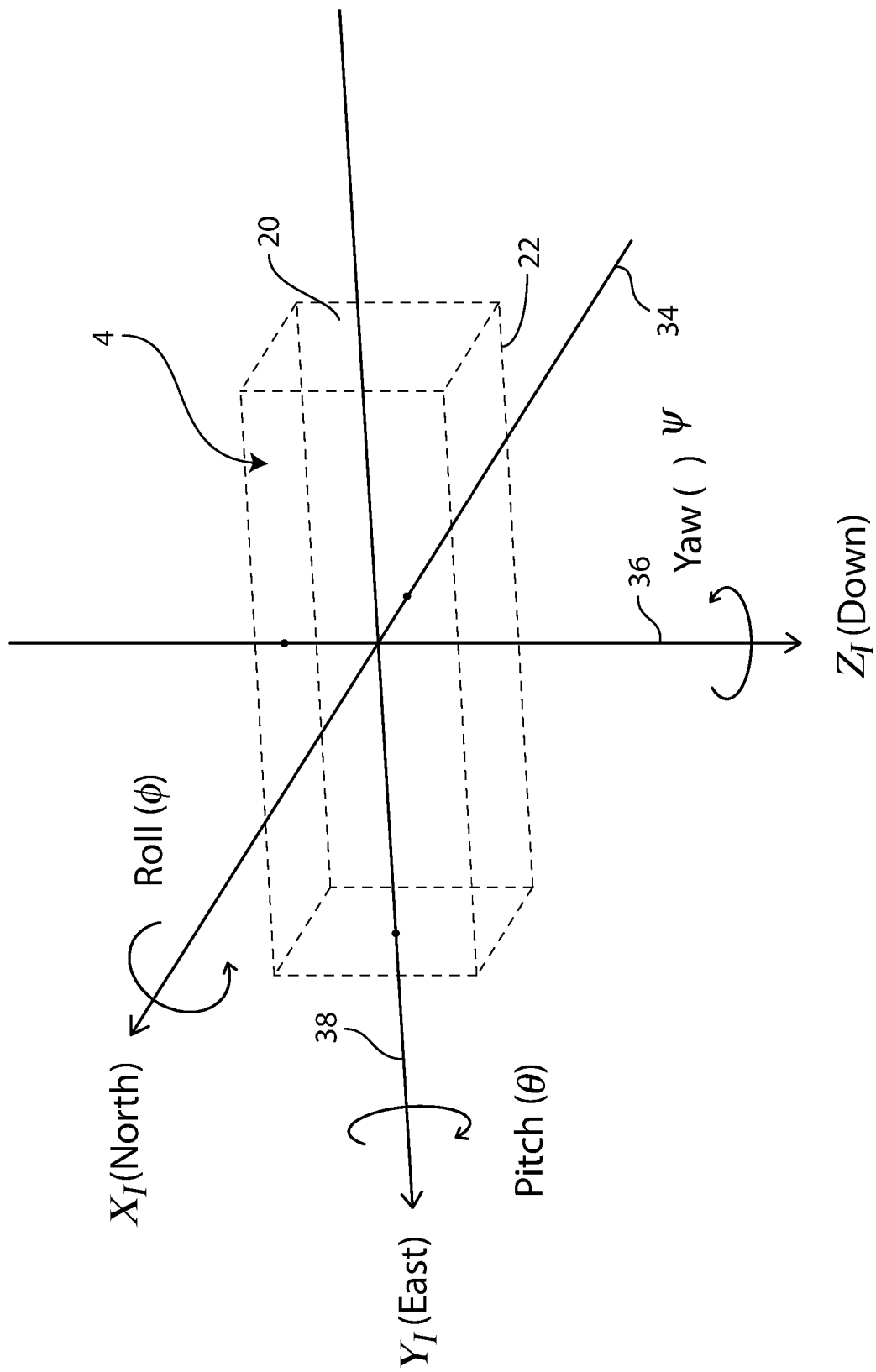
FIG. 4 is an isometric view of a camera illustrated with axes defining three degrees of rotational movement.

FIG. 1 illustrates a photographer moving a camera transversely while maintaining a monopod foot in position. FIG. 2 is an illustration of the photographer utilizing the apparatus and system according to the present subject matter to provide desired pitch of a supported camera. FIG. 3 is an illustration of the photographer utilizing the apparatus and system according to the present subject matter to select yaw of a supported camera. FIG. 4 is an isometric view of a camera illustrated with axes defining three rotational degrees of freedom. FIG. 1, FIG. 2, FIG. 3, and FIG. 4 are taken together. In the arts of cinematography, videography, and photography with virtually any viewing device, a significant requirement is maintaining a level image horizon and/or consciously maintaining an "off level" shot known in the cinema industry as a "dutch tilt."

In FIGS. 1, 2, and 3 a photographer 1 utilizes her hands 2 to operate a camera 4 supported via a mounting head 6 to a monopod 8. The monopod 8 comprises an axial rod 10 having an axis 11. A monopod base 12 is at the lower end of the monopod 8. Operating the camera 4 includes positioning the camera to obtain a particular field of view desired by the photographer 1. The term "camera" is used in its broad sense to denote a device that collects radiation and sends the radiation to a sensor. The camera 4 may be a still camera or a motion picture camera. The sensor may comprise photographic film or charge coupled device (CCD) sensors. Other applications could make use of the present subject matter in the future. For example, the camera 4 could comprise a scintillator or a Raman spectroscopy probe or other device not currently considered to be a camera. The camera 4 comprises a body 20 and a lens 22. The camera body 20 has a vertical dimension 24, which is vertical when the camera 4 is positioned to provide a level horizon. In the present illustration, the camera 4 is a still camera. Opposite lateral sides of the camera 4 comprise a first grip 26 and a second grip 28. In the present illustration, the grips 26 and 28 simply comprise lateral sides of the camera body 20. In larger cameras, the grips 26 and 28 may comprise handles that can be securely grasped by the hands 2.

FIG. 4 is an isometric view of a camera illustrated with axes defining three degrees of rotational movement. The photographer 1 moves the camera 4 through successive angular displacements about rotational axes. References to axes and angles refer to orientations illustrated in FIG. 4. An X axis 34 may be viewed as an axis normal to and intersecting a Z axis 36. In the present illustration, the Z axis 36 comprises a vertical line. The Z axis 36 could conceivably be nonvertical. However, most embodiments will regard the Z axis 36 as being vertical. Rotation of the camera body 20 around the X axis 34 comprises roll. Angular displacement of roll from a reference position is measured by angle φ. A Y axis 38 is coplanar with the X axis 34 and perpendicular to the Z axis 36. Rotation of the camera body 20 around the Y axis 36 comprises pitch. Angular displacement of pitch from a reference position is measured by angle θ. Yaw comprises rotation of the camera body 20 around the Z axis 36. Angular displacement of yaw from a reference position is measured by angle ψ.

In use, the mounting head 6 (FIGS. 1, 2, and 3) provides the photographer 1 with the support of the monopod 8. At the same time, the mounting head 6 permits rotation in the three rotational degrees of freedom as illustrated in FIG. 4, namely roll, pitch, and yaw. In operation, a level horizon may be maintained by relative angular motion between the camera 4 and the monopod 8. The relative angular motion occurs when the photographer 1 leans the camera 4 into different angular positions in order to point the camera 4 in a desired direction. The photographer 1 has the ability to maintain a substantially constant horizon even as the angular disposition of the monopod 8 changes in response to motion by the photographer 1. The value of angular displacement φ of roll and angular displacement θ of pitch may be measured between the monopod 8 and the bottom surface of the camera body 20. The angle of yaw is measured with respect to a reference position.

FIG. 1 illustrates the photographer 1 moving the camera 4 transversely while maintaining the monopod base 12 in position. In this matter, a steadiness of the position of the camera 4 is enhanced. The mounting head 6 permits the camera 4 to roll about the X axis 34 (FIG. 4). Were the camera 4 mounted directly to the monopod 8 along the axis of the rod 10, the horizon of the camera 4 would be tilted. However, the mounting head 6 allows for the monopod 8 to be angularly displaced with respect to the camera body vertical dimension 24 (FIG. 3). The roll angle φ is measured between the Z axis 36 and the resulting angular position of an axis of the axial rod 10.

Pitch is demonstrated in FIG. 2. Pitch is the angular displacement from the X-Y plane. Pitch is varied by an angle θ as rotation of the camera body 20 with respect to the Y axis 38. Yaw is demonstrated in FIG. 4 in which the photographer 1 rotates the camera 4 about the Z axis 36. The value of the angular displacement around the Z axis 36 is equal to the value of angular displacement ψ about the monopod axis 11.

Figure 5:
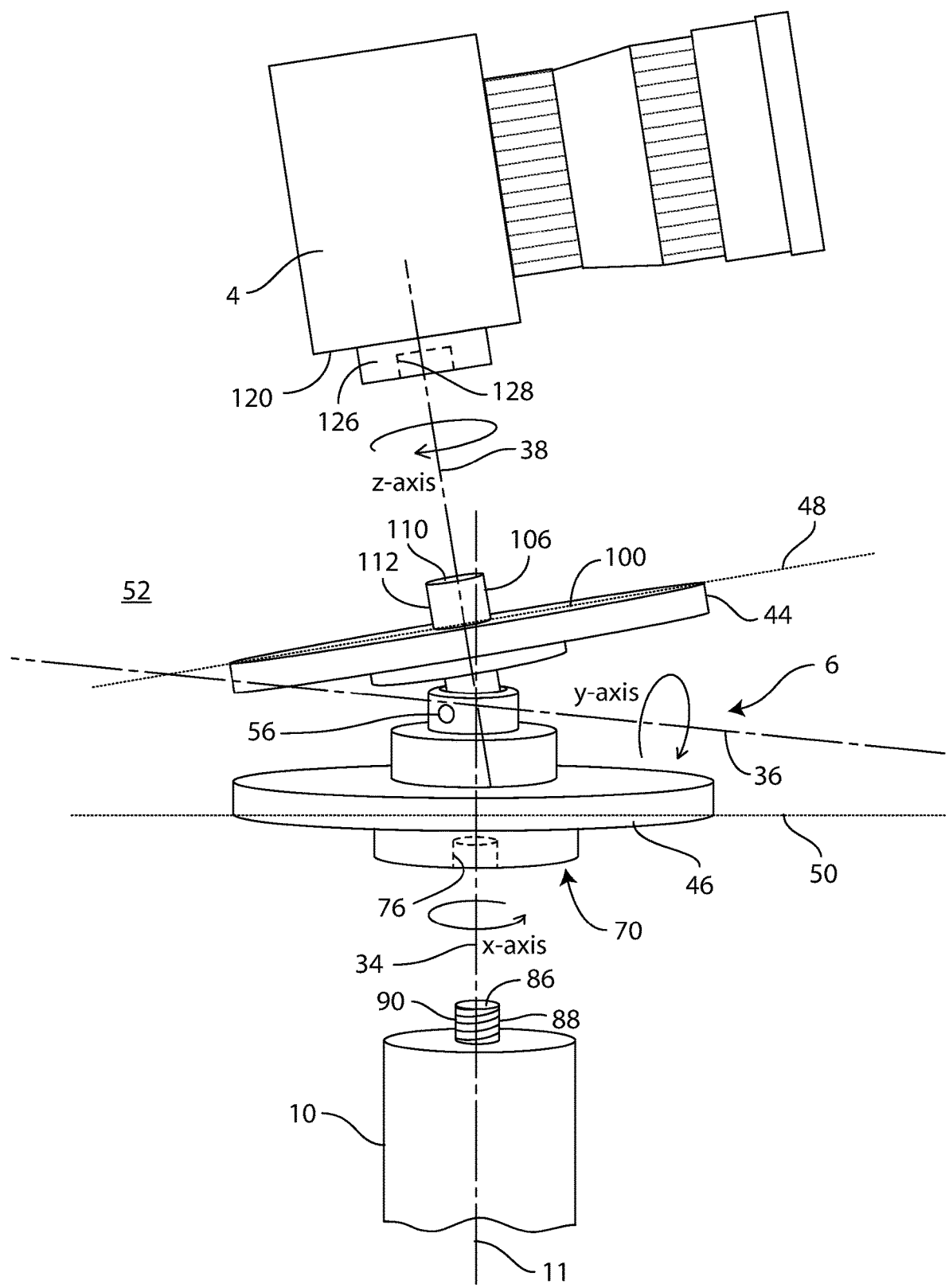
FIG. 5 illustrates components comprising systems according to the present subject matter.

FIG. 5 is a perspective view of an assembly 52 including the systems and apparatus according to the present subject matter. The camera 4, mounting head 6, and the monopod 8 are illustrated in axial alignment. One apparatus is the mounting head 6. One system comprises the mounting head 6 mounted to the monopod 8. Another system comprises the mounting head, the monopod, a camera with the mounting head having proper locking mechanisms. The construction of and interactions between system components are described with respect to FIG. 6, FIG. 7, and FIG. 8. The overall view of the apparatus and systems is provided in FIG. 5.

FIG. 5 illustrates a simplified form of mounting head 6. Further details of the mounting head 6 are described below. The mounting head 6 comprises an upper head assembly 44 and a lower head assembly 46. The upper head assembly 44 has an upper surface plane 48. The lower head assembly 46 has a lower surface plane 50 The upper head assembly 44 and the lower head assembly 46 are mounted to permit simultaneous, continuous variations in roll and pitch of the upper surface plane 48 with respect to the lower surface plane 50. This mounting may also permit variation in yaw. In a nominal rest position, the upper surface plane 48 and the lower surface plane 50 are substantially parallel. The upper head assembly 44 and the lower head assembly 46 are coaxially mounted and axially displaced along a vertical mounting head axis 54.

A swivel bearing 56 is supported radially inwardly of, i.e., axially intermediate, the upper head assembly 44 and the lower head assembly 46. In one form the swivel bearing is a unique stainless steel ball joint. The stainless steel ball joint prevents the casings from separating. Both top and bottom plates, with their male and female mounting threads, are designed within the stainless steel module. The ball joint prevents separation of the top and bottom plate but also prevents separation between the camera and monopod. It is not unusual for a professional cinematographer to use a camera costing $200,000.00. Reliably preventing separation is a distinct advantage.

The swivel bearing 56 is a component which allows simultaneous variations in roll and pitch of the upper surface plane 48. The swivel bearing 56 is described in greater detail with respect to FIG. 12. The swivel bearing 56 functions as a universal joint. The swivel bearing 56 provides this function in a reliable, simplified, cost-effective manner. The swivel bearing 56 could comprise a pivoted articulated arm.

A resilient block 80 is located between the upper head assembly 44 and the lower head assembly 46 and may be rest in the lower head assembly 46. The resilient block 80 may comprise a block of resilient material or a spring assembly. Compression performance may be measured by a crush or squeeze rate in units of inch lbs. One suitable material for the resilient block 80 comprises urethane rubber. Another form of resilient block 80 comprises garnet and rubber acting as a spring. Spring rates associated with various resilient materials will inform the selection of the material to be used.

Different viscosities of the resilient block 80 determine the amount of flex needed for horizon correction. Each viscosity is different commensurate with weight of the viewing device, e.g., the camera 4. Different resilient blocks 80 may each be provided to accommodate a different range of camera weights. All similar in size, each mounting head 6 is identified by its inner viscosity. One inner viscosity may accommodate such cameras as a DSLR camera weighing under five pounds. Another resilient block 80 may accommodate a medium sized camera, weighing between ten pounds and twenty pounds. A cinema camera, weighing over 20 pounds may be accommodated by another resilient block 80. For example, when using a lightweight DSLR camera attached to a monopod a thinner viscosity would be necessary allowing the operator greater ease finding horizon. With a heavier viscosity being "off level" and finding horizon would be difficult. The heavier weight, e.g., a 35 pound camera, would require a heavier viscosity within the mounting head 6. If too light the viewing device or camera would hobble especially with a higher center of gravity increasing a pendulum effect. Therefore, the weight of the camera or viewing device determines the density and viscosity of the weight to the object being supported. It is then, through the correction of the operator, slight tilting with minimal force left or right the operator would find level within seconds.

The resilient block 80 interacts to respond to pressure when the lower head assembly 46 is tilted with respect to the upper head assembly 44, as by tilting the monopod 8. The resilient block 80 is designed in accordance with the present subject matter to provide a selectable resistance and a selectable relationship between force applied to the mounting head 6 by a photographer 1 to the camera 4. The mounting head 6 may be designed to have a selectable degree of linearity in force applied versus displacement of the monopod 8 through various degrees of freedom. A photographer may desire to have the same degree of force required for displacing a camera through angular displacements of different values. It is generally desirable to provide increasing nonlinear resistance toward limits of displacement of the mounting head 6. An elastic modulus range may be selected to provide a given feel while using a camera 4 of a particular weight. Operation is also selectable by means of preloading the resilient block 80. Preloading determines an initial effective tension exerted between the upper cup 140 and the lower cup 150. A torque loading table may be used to describe response of the resilient block 80 to rotation of the swivel bearing 56.

The mounting head 6 aids the photographer 1's ability to shoot verite, without the burden of carrying weight to obtain horizon level instantly. Other advantages of using the mounting head 6 would be to create a cinema verite style.

The lower head assembly 46 comprises a lower mounting surface section 70. The lower mounting surface section 70 comprises releasable securing means 76. The releasable securing means 76 may be an internal, female thread 78 in an industry standard diameter and pitch. The monopod 8 comprises a monopod upper mounting surface 86. The upper mounting surface 86 also comprises releasable securing means 88. The releasable securing means 88 preferably comprises a mounting bolt 90 having an industry standard diameter and pitch for mating with the releasable securing means 76.

The upper head assembly 44 comprises an upper mounting surface section 100 which includes releasable securing means 106. The releasable securing means 106 may comprise a bolt 110 having an external male thread 112 in an industry standard diameter and pitch. The releasable securing means 106 mates with a lower mounting surface 120 of the camera 4. The lower mounting surface 120 includes releasable securing means 126 such as a female thread 128 in an industry standard diameter and pitch. Different industry standard diameters and pitches are available for general correspondence to size and weight of equipment. In one nominal embodiment, the bolt 110 has a ¼ inch diameter with a 20 pitch male thread. The lower mounting surface section 70 has a ⅜ inch internal female thread 78 with a 16 pitch thread. Standard releasable fastening means are provided by manufacturers so that different cameras may be interchangeably used with a particular support, for example. Nominal thread depths range from 0.100" to 0.750".

In use the bolt 110 at the upper surface of the mounting head 6 is fastened to the releasable securing means 126 on the camera 4. The female thread 128 and the external male thread 112 lock axially. The bolt 110 is mechanically connected to the upper cup 140. Consequently, the upper cup 140 is prevented from spinning around the bolt 110. Removal of the camera 4 can be reliably accomplished.

This structure provides the capability to simultaneously adjust pitch and roll of the camera 4 while maintaining a substantially constant horizon. The resilient block 80 provides a degree of resistance to motion in order to facilitate the photographer 1's control over displacement of the camera 4. Jerky or shaky motions are substantially prevented. Consequently, these motions will not be visible in the captured images. After being compressed, the resilient block 80 exerts a force between the upper head assembly 44 and the lower head assembly 46. As the photographer 1 eases pressure on the camera 4, potential energy in a compressed portion of the resilient block 80 tends to push the camera 4 to return to its level, center position with rebound force. Because the mounting head 6 permits simultaneous motion within a plurality of degrees of freedom, the photographer 1 need not move her hands 2 with respect to the camera 4. Consequently, the photographer 1's control over the camera 4 is maximized. In this manner, the photographer 1 may concentrate on following a scene without distraction of having to move her hands 2.

It is important to provide for nesting of components since compactness is required in normal operation. Geometry for particular elements is considered so that components may interact successfully under heavy loads with a long lifecycle.

Figure 6:
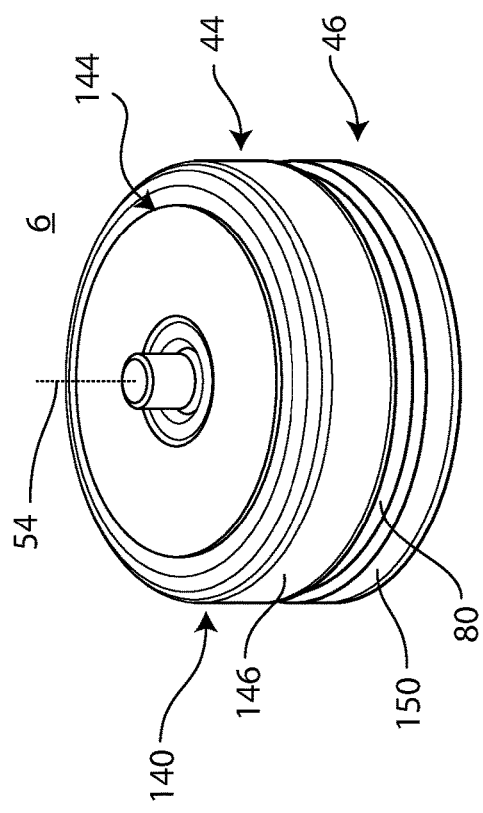
FIG. 6 is an isometric view of one form of a mounting head.
Figure 8:
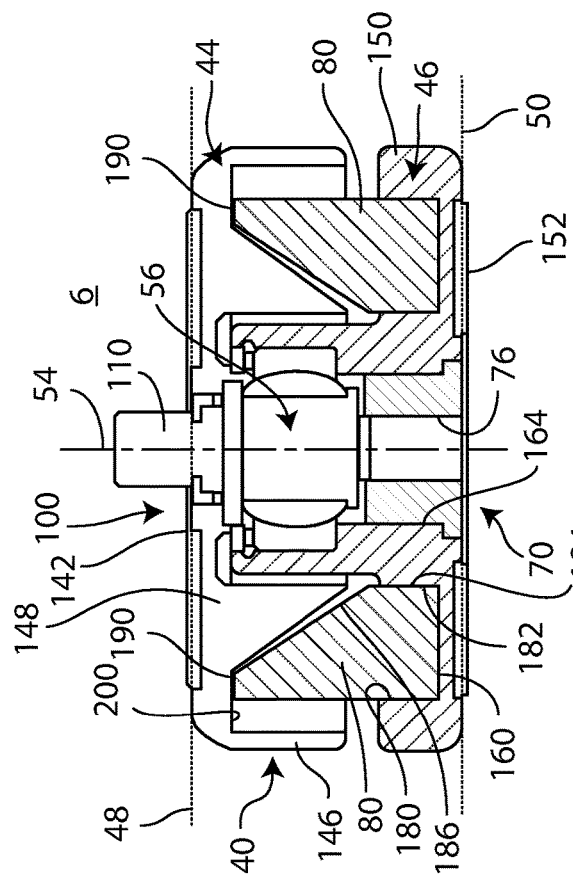
FIG. 8 is a cross section taken along line 8-8 of FIG. 7.
Figure 7:
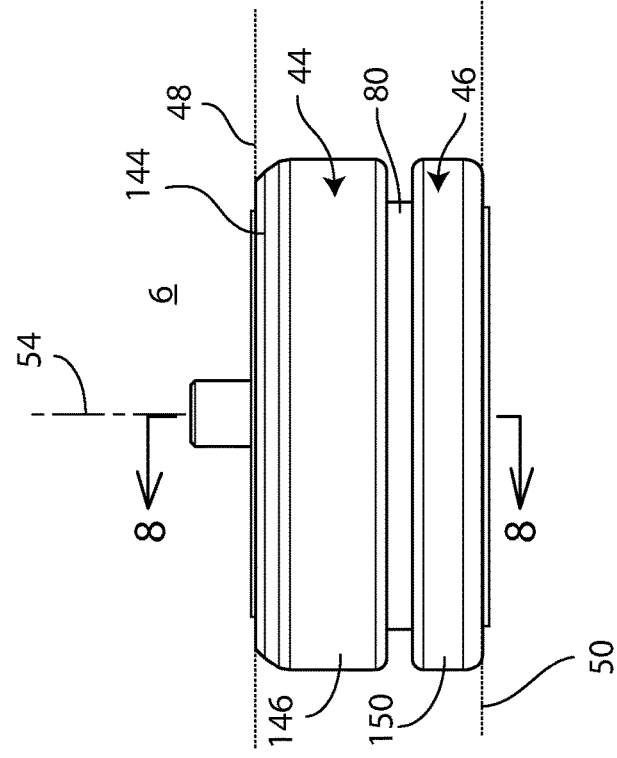
FIG. 7 is an elevation of the mounting head.

FIG. 6 is an isometric view of one preferred form of the mounting head 6. FIG. 7 is an elevation of the mounting head 6. FIG. 8 is a cross section taken along line 8-8 of FIG. 7. FIG. 6 through FIG. 8 are taken together.

As seen in FIGS. 6-8, the mounting head 6 comprises the upper head assembly 44 and the lower head assembly 46. The upper head assembly 44 may be formed as an upper cup 140 having an annular upper surface 144 surrounding a central aperture 142. The lower head assembly 46 may be formed as a lower cup 150 having an annular lower surface 152 surrounding a lower central aperture 154. The upper cup 140 and the lower cup 150 are coaxially mounted and may each have the same outer diameter. The upper cup 140 comprises a cylindrical sleeve 146 axially extending toward the lower cup 150. The upper cup 140 further comprises a concentric, radially extending inner wall 148. Axial distance between the annular upper surface 144 and the annular lower surface 152 is selected to allow housing of a desired resilient block 80. The upper cup 140 and the lower cup 150 are proportioned to leave an extent of the resilient block 80 exposed. When the mounting head 6 is tilted, the edges of the upper cup 140 and the lower cup 150 will interfere, defining a limit of angular displacement. As further described below, the cross section of the inner wall 148 is formed to provide a preselected interaction with the resilient block 80. In the present illustration, the inner wall 148 has a triangular cross section.

As best seen in FIG. 8, the resilient block 80 is supported to an annular radial inner wall 160 of the lower cup 150. The radial wall 160 provides an equal and opposite force against forces applied to the resilient block 80 in the axial direction. In the present illustration, the resilient block 80 has an axially extending outer wall 180 and an axially extending inner wall 182. The inner wall 182 comprises a first surface 184 having an inner diameter surrounding the interior sleeve 164. A radially extending upper block surface 190 faces an axially inner surface 200 of the upper cup 140.

A reaction surface 186 extends between the upper block surface 190 and the inner wall 182. As further described below, the reaction surface 186 cooperates with the inner wall 148 to provide variable resistance in response to varying degrees of tilt of the monopod 8. Having the reaction surface 186 that is angled with respect to the Z axis reacting against the surface of the inner wall 148, which is also an angle with respect to the Z axis, tends to provide linear response. Differing shapes of the resilient block 80 will vary damping performance of the mounting head 6.

Factors describing the performance of the mounting head 6 include maximum angular displacement, speed of angular displacement, speed of recovery, and displacement with respect to weight of the camera 4. In accordance with the subject matter, it has been found that performance of the mounting head 6 is affected by several parameters. One such parameter is pivot altitude. The pivot altitude is the location on the vertical mounting head axis 54 of the effective pivot point of the swivel bearing 56. A pivot plane intersects the effective pivot point of the swivel bearing 56. Another parameter is the elastic modulus of the resilient block 80 and the spring rate provided by the resilient block 80. The composition of resistive material, sizes of components, shapes of components, and preloading on the resilient block 80 all affect performance.

FIGS. 6, 7, and 8 illustrate the mechanism for interfacing the mounting head 6 to the monopod 8 for interaction to maintain a level horizon. This interaction permits the upper surface plane 48 of the mounting head 6 to remain substantially horizontal as the monopod 8 is tilted. Further, the mounting head 6 interfaces the camera 4 to the combination of the mounting head 6 and the monopod 8. By moving the camera 4, the photographer 1 applies force via the mounting head 6 to move the top of the monopod 8 with respect to a fixed position of the monopod base 12.

The mounting head 6 is a discrete apparatus. This is an apparatus that provides the ability to maintain a level horizon of an upper level plane while pitch and roll of an object coupled to the apparatus may continually and simultaneously change.

A first system comprises the mounting head 6 in combination with the monopod 8. This first system provides the ability to move an upper part of a monopod 8 coupled to the mounting head 6 in three-dimensional space while maintaining the upper plane 48 of the mounting head 50 on a substantially level horizon or on a different horizon as selected by the photographer 1.

A second system comprises the mounting head 6 in combination with the monopod 8 and further in combination with the camera 4. In this system, force is applied by the photographer 1 to the camera 4. The monopod 8 supports the camera 4 while allowing the photographer one freedom of motion. The camera 4 maintains a level horizon while the photographer 1 has significant freedom of movement. The second system further comprises proper locking mechanisms to maintain the camera 4 and the monopod 8 in reliable engagement with the mounting head 6.

Figure 9:
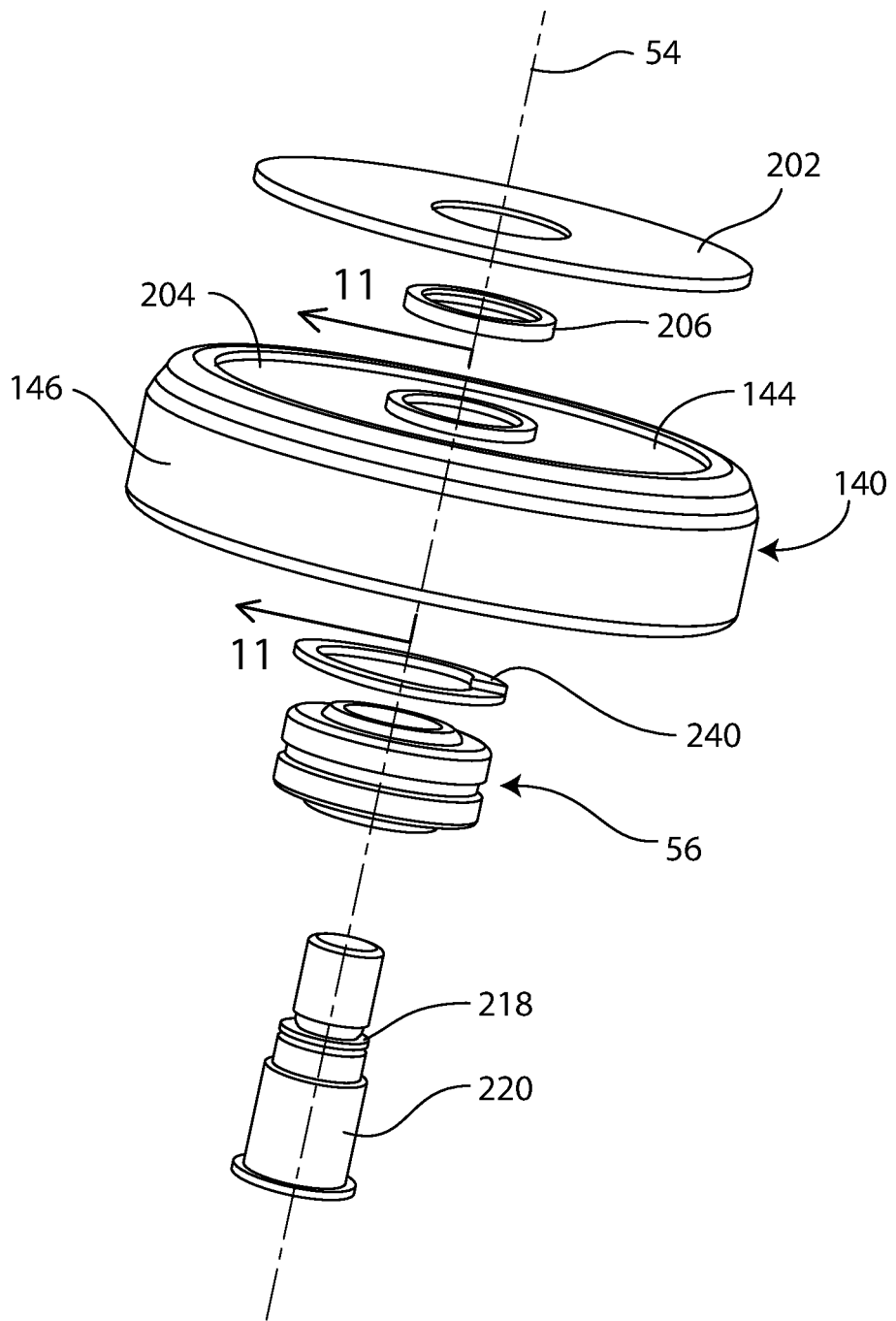
FIG. 9 an exploded isometric view of an upper head assembly.
Figure 10:
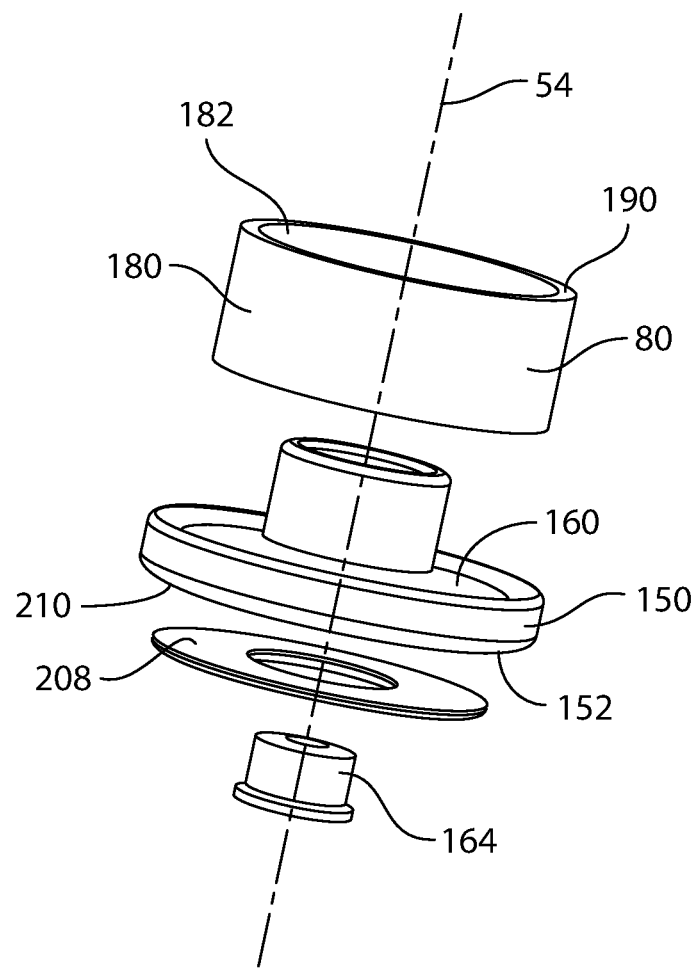
FIG. 10 is a partial, exploded isometric view of a lower head assembly.
Figure 11:
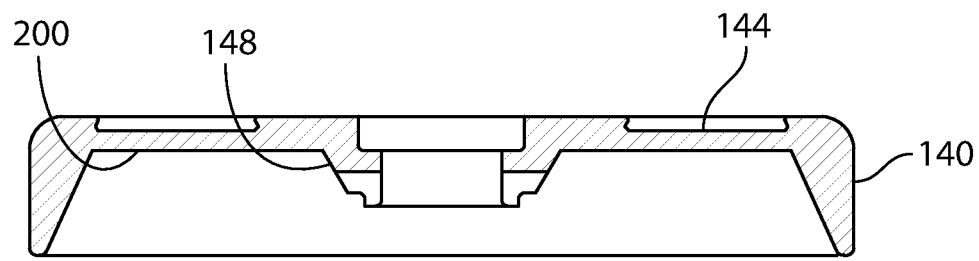
FIG. 11 is a cross section taken along line 11-11 of FIG. 9.

FIG. 9, FIG. 10 and FIG. 11 further illustrate the structure of FIG. 6, FIG. 7, and FIG. 8. FIG. 9 is an exploded isometric view of components of the upper head assembly 44. FIG. 10 is a partial, exploded isometric view of components of a lower head assembly 46. FIG. 11 is a cross section taken along line 11-11 of FIG. 9. In FIG. 9 through FIG. 11, the same reference numerals are used to denote components corresponding to those in FIG. 6 through FIG. 8. However, the embodiment of FIG. 9 through FIG. 11 represents one of many alternative forms of mounting head that may be provided in accordance with the present teachings. The resilient block 80 takes a different form from that illustrated in FIG. 8. The inner wall 148 of the upper cup 140 has a different shape in FIG. 11 from that in FIG. 8. The embodiment of FIG. 11 provides for interaction of the resilient block 80 with the inner wall 148 which does not include reaction of one canted surface against another.

The elements in FIGS. 9-11 are disposed along the vertical mounting head axis 54. An upper slip ring 202 is received in an upper recess 204 in an upper surface of the upper cup 140. A retaining ring 206 is disposed between the upper slip ring 202 and the upper cup 140 to receive and snap into a groove 218 in the axial support member 220. A lower slip ring 208 fits in a lower recess 210 on a lower surface of the lower cup 150. The interior sleeve 164 projects through the lower slip ring 208 and is received in the lower cup 150. A retaining ring 240 is placed intermediate the upper cup 140 and the swivel bearing 56. The retaining ring 240 retains the axial support member 220 against the swivel bearing 56. The upper slip ring 202 prevents galling between the upper head assembly 44 and the camera 4 or other equipment. The lower slip ring 220 prevents galling between the lower head assembly 46 and the monopod 8. In FIG. 11, the inner wall 148 substantially comprises a rim rather than a conical projection as in FIG. 8. The action of the resilient block 80 will occur to a greater extent with the inner surface 200 of the upper cup 140 rather than with the inner wall 148.

The resilient block 80 may take a number of forms of resistive material. These forms include resilient rings, springs, and annular sacks. Different configurations of resistive material may be selected to provide corresponding interactions within the mounting head 6. These are further described with respect to FIGS. 13-15 below.

Figure 12:
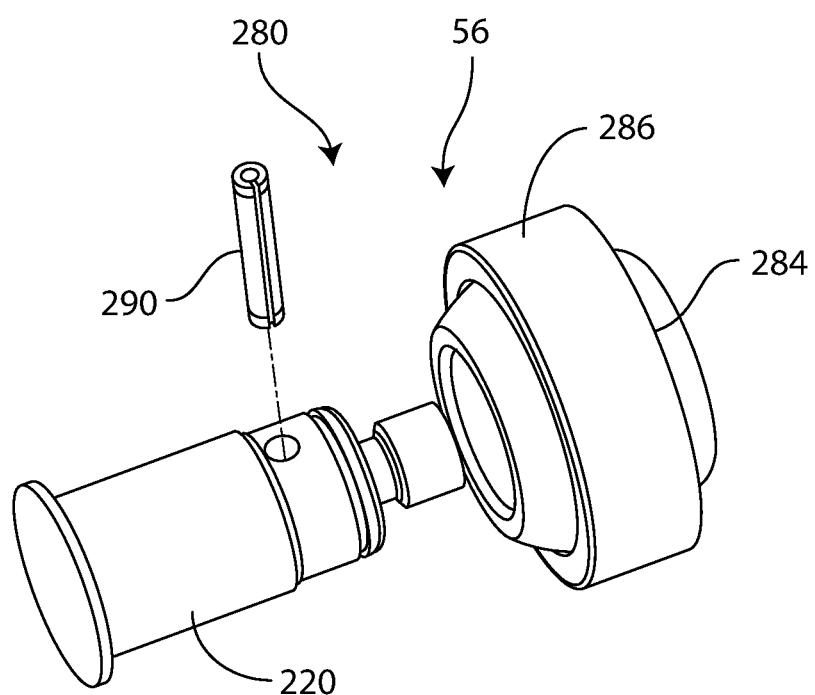
FIG. 12 is an exploded isometric view of a universal support.

FIG. 12 is an exploded isometric view of a universal support 280. The universal support 280 comprises a centrally located pivot between the upper head assembly 44 and the lower head assembly 46. The universal support 280 comprises the axial support member 220 and the swivel joint 56. The swivel joint 56 comprises an inner bearing 284 and an outer bearing 286. The universal support 280 is assembled by sliding the swivel joint 56 axially over the axial support member 220 and constraining the swivel joint 56 from further axial motion by a cotter pin 290. The inner bearing 284 is rigidly constrained with respect to roll and pitch. The outer bearing 286 moves universally with respect to the inner bearing 284. The upper head assembly 44 and more particularly the upper cup 140 is supported to the outer bearing 286. Motion of the lower cup 150 with respect to the upper cup 140 is freely allowed by the swivel joint 56 and is damped by the resilient block 80. The universal joint 280 can be built with a two-piece or more universal joint or equivalent.

Other forms of the universal support may comprise a flexible member. A flexible member could comprise a cable, carbon fiber, or an articulated support. A flexible member does not have a discrete pivot point. Bending of the flexible member will result in deflection about an effective pivot point.

Figure 13:
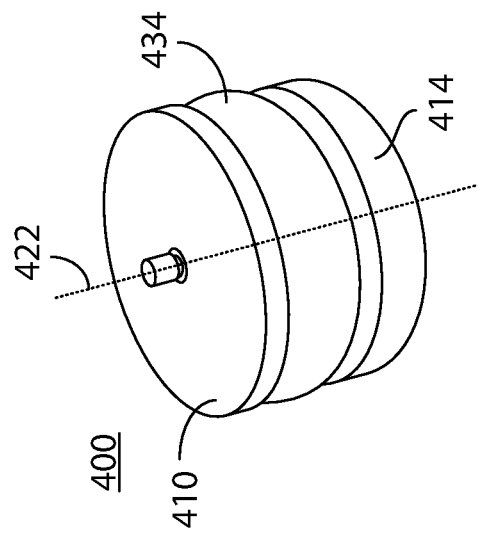
FIG. 13 is an isometric view of a block test apparatus.
Figure 15:
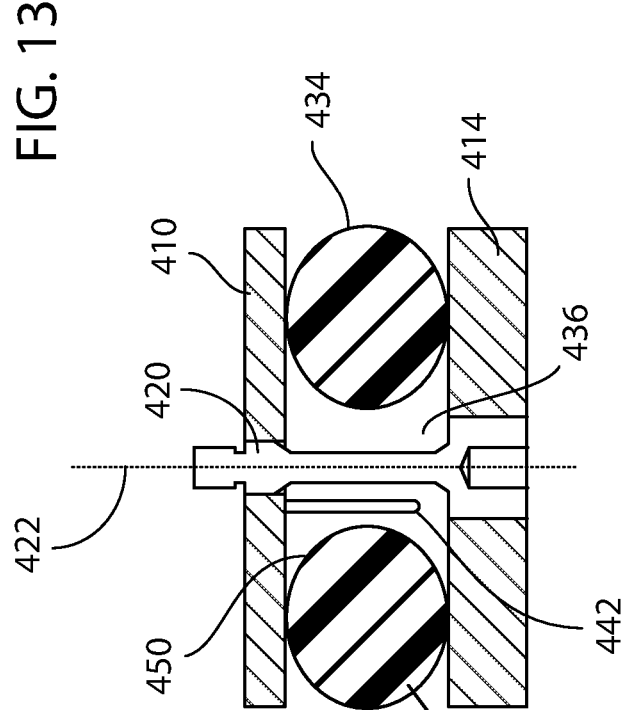
FIG. 15 is a cross sectional view taken across line 15-15 of FIG. 14.
Figure 14:
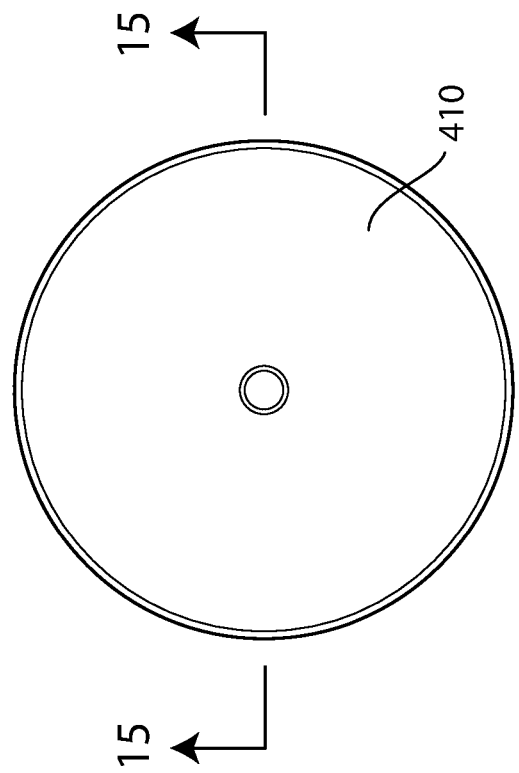
FIG. 14 is a plan view of the block test apparatus.

FIGS. 13-15 illustrate a block test apparatus 400. FIG. 13 is an isometric view of the block test apparatus 400. FIG. 14 is a plan view of the block test apparatus 400. FIG. 15 is a cross sectional view taken along line 15-15 of FIG. 14. An upper plate 410 is maintained in position with respect to a lower plate 414 by a flexible axial support member 420. The upper plate 410 and the lower plate 414 may each be circular and maintained in parallel when at rest. Other shapes may be used. The upper plate 410 receives compressive force corresponding to force applied from a camera to a mounting head. The flexible axial support member 420 has an axis 422 The axial support member 420 may be articulated by a joint or through flexure. A resistance member 434 is mounted intermediate the upper plate 410 and the lower plate 414 in a resistance zone 436.

In order to construct a mounting head, the resistance member 434 needs to be proportioned to desired operating characteristics and the equipment which it will be coupled to. The following description defines for those skilled in the art precisely how the desired relationship can be determined.

A first inner surface 442 may be provided as a surface to which the resistive material 434 will react. The first inner surface 442 may be integral with the upper plate 410 or otherwise secured in the block test apparatus 400. A second inner surface 450 is a surface of the resistive member 434. In a mounting head, surfaces corresponding to the first inner surface 442 and the second inner surface 450 may be provided in positions for interaction to vary operation of the mounting head. Shapes of the first and second inner surfaces 442 and 450 need not be the same. In one preferred form, the shape of the first inner surface 442 may comprise an inclined plane with respect to the axis 422. Other shapes may be used. This selected shape will affect angular displacement of the upper plate 410 versus force with respect to the axis 422.

Calculations with respect to resilient material in the resistance zone 436 may utilize measurements in terms of volume or in terms of specific dimensions of a test resilient block. Many different combinations of dimensions can provide similar results. In various nominal embodiments used to support commonly used cameras, volume of the resistance zone 436 has a range of 0.2 to 500 cubic inches. The volume needed to provide desired performance is a function of the weight of the camera, the moment of force produced in response to movement of the camera by a camera operator, the shape and durometer of the resistive material 434, and the speed and degree of compensation to be provided. The moment of force will be greater for cameras that will have a high center of gravity in relation to a mounting head. For a given level of deflection, the resistance member 434 must have a greater hardness than for similar damping for a camera with the same weight but having a lower center of gravity.

The resistance member 434 comprises compressible, resilient material 438. The resistance member 434 may comprise, for example, rubber, metal, or plastic springs, or granular material in a container. In the present illustration, the resistance member 434 is toroidal, i.e. a torus or a shape fitting within the envelope of a torus. Preloading on the resistance member 434 may be determined by the axial distance between the upper plate 410 and the lower plate 414. Depending on desired performance, materials having a durometer of 0 to 100 may be used. Solid materials may be used. In another form, a flexible cover may be filled with compressible material. Alternatively, the resistance member 434 could comprise a leaf spring construction or an enclosed liquid.

Pivot altitude must be considered in designing a mounting head. The pivot altitude depends on the resilient material 438. Other dimensions are considered. Axial length of the resistance member 434 needs to be considered. Generally, it is desired to minimize the distance between the camera and the support device created by the mounting head. Diameter of the mounting head needs to be reasonably related to dimensions of the support and dimensions of the camera.

In order to test a material, a resistance member 434 is placed in the resistive material zone 436. Omnidirectional movement such as roll or pitch or combinations thereof are applied via the upper and lower plates 410 and 414 to the resistive material 434. As roll or pitch is induced into the test apparatus 400, displacement of the resilient material 438 takes place. A downward compression force compresses the resilient material 438 in the axial degree of freedom and also displaces resilient material radially. The effect of compression is a function of the shape of the resistance member 434. In one form, determination of the shape and composition of the resistance member 434 may be determined empirically. More specifically, a designer may select compositions and shapes for the resistance material 434. These configurations are tested to determine performance. The parameters determined to be satisfactory are provided to a manufacturer of a resistance member 434 for inclusion in manufactured mounting heads. Sensors 460 are positioned to measure response of the resistance member 434 to forces applied via the upper and lower plates 410 and 414.

The purpose of the test apparatus 400 is to provide a definition of "suitable" designs of a resistance member 434 for a given configuration of a mounting head operating with a camera, a support such as a monopod, or both.

Those skilled in the art may wish to use alternative materials or designs. In accordance with the present subject matter, it has been established that a relationship between pivot altitude, elastic modulus, diameter of components, size of features, preloading, angle of push surface, size and shape of deformation cavity are each a contributing factor to performance characteristics. Embodiments may be designed to keep the force required to induce roll or pitch consistent in pressure as angular displacement increases with respect to a horizontal axis. The design is manufacturable and cost-effective.

Although the foregoing description has specified certain steps and materials that may be used in the method of the present invention, those skilled in the art will appreciate that many modifications and substitutions may be made. Accordingly, it is intended that all such modifications, alterations, substitutions, and additions be considered to fall within the spirit and scope of the invention as defined by the appended claims. Thus the present invention is not limited to the structures described herein.

The invention claimed is:

1. A mounting head for maintaining a preselected angular spatial relationship of a supported device and a supporting device, whereby a selected horizon may be maintained for the supported device, comprising:

a. an upper head assembly having releasable securing means for connection to a supported device and maintaining a fixed angular relationship with the supported device, said upper head assembly defining an upper plane;
b. a lower head assembly having releasable securing means for connection to a supporting device, said lower head assembly defining a lower plane;
c. a universal joint interconnecting said upper head assembly and said lower head assembly, said universal joint providing for variation in roll and pitch between said upper plane and said lower plane;
d. a compressible resilient member housed between said upper head assembly and said lower head assembly, said resilient member being dimensioned to maintain said upper plane and said lower plane in a preselected angular relationship at rest, said resilient member having at least one physical parameter having a value selected to provide a selected resistance to relative motion between said upper head assembly and said lower head assembly; and
e. said upper head assembly comprising a coupling to receive external force from a user.

2. The mounting head according to claim 1 wherein properties of said resilient member is a member whose suitability is determined by testing in a mounting head test fixture.

3. The mounting head according to claim 1 wherein said resilient member comprises an elastomeric material shaped to fit within a toroidal envelope.

4. The mounting head according to claim 3 wherein said resilient member comprises urethane rubber.

5. The mounting head according to claim 1 wherein said upper head assembly and said lower head assembly respectively comprise a first cup and a second cup, each cup having an axial end with a radially extending face, and being dimensioned to expose a preselected axial length of said resilient member.

6. The mounting head according to claim 5 wherein said lower head assembly comprises a lower mounting surface section which includes releasable securing means.

7. The mounting head according to claim 6 wherein said upper head assembly comprises an upper mounting surface section which includes releasable securing means.

8. The mounting head according to claim 7 wherein said universal joint comprises a swivel bearing.

9. The mounting head according to claim 7 wherein said universal joint comprises a flexible member having an effective pivot point.

10. The mounting head according to claim 8 wherein said resilient member comprises an elastomeric material shaped to fit within a toroidal envelope.

11. The mounting head according to claim 8 wherein said resilient member comprises an annular block having an angled surface and wherein said upper cup comprises an annular wall radially inwardly of said angled surface and in axial registration with said angled surface and positioned so that said angled surface bears against said annular wall in response to external force applied to said mounting head.

12. The mounting head according to claim 6 wherein said releasable securing means comprises a threaded coupling.

13. A system for use in allowing angular displacement between a mounting head and a tiltable support comprising:
a. the mounting head;
b. the tiltable support;
c. a first interactive coupling comprising a first member on said mounting head and a second member on said tiltable support, the interactive coupling releasably securing said mounting head to said tiltable support;
d. an upper head assembly having releasable securing means for connection to a supported device and maintaining a fixed angular relationship with the supported device, said upper head assembly defining an upper plane;
e. a lower head assembly comprising said first member, said lower head assembly defining a lower plane;
f. an omnidirectional universal joint interconnecting said upper head assembly and said lower head assembly, said universal joint providing for variation in roll and pitch between said upper plane and said lower plane; and
g. a compressible resilient member housed between said upper head assembly and said lower head assembly, said resilient member being dimensioned to maintain said upper plane and said lower plane in a preselected angular relationship at rest, said resilient member having at least one physical parameter having a value selected to provide a predetermined resistance to relative motion between said upper head assembly and said lower head assembly.

14. The system according to claim 13 wherein said tiltable support comprises a monopod.

15. The system according to claim 13 wherein said first member comprises a bore having a female thread and said second member comprises a bolt having a male thread, the female thread having a bottom thread locked axially to a top thread of the male thread.

16. The system according to claim 15 further comprising a camera mounted to said upper head assembly, a second interactive coupling comprising a first member on said camera and a second member on said mounting head, the second interactive coupling releasably securing said camera to said mounting head.

17. The system according to claim 16 wherein said camera is mounted to said mounting head to transmit force applied by a user to said camera through said mounting head to said monopod.

* * * * *